(12) United States Patent
Yao et al.

(10) Patent No.: US 7,597,012 B2
(45) Date of Patent: Oct. 6, 2009

(54) SYSTEM AND METHOD FOR USING A SPRAY/LIQUID PARTICLE COUNT (LPC) TO MEASURE PARTICULATE CONTAMINATION

(75) Inventors: Yi Zhao Yao, Singapore (SG); Hui Yan Hu, Singapore (SG); Shaoyong Liu, Singapore (SG); Kelvin Ang Kor Seng, Singapore (SG); Garvin J. Stone, San Juan Bautista, CA (US); Gina M. Whitney, San Jose, CA (US)

(73) Assignee: Hitachi Global Storage Technologies Netherlands B.V., Amsterdam (NL)

( * ) Notice: Subject to any disclaimer, the term of this patent is extended or adjusted under 35 U.S.C. 154(b) by 248 days.

(21) Appl. No.: 11/454,750

(22) Filed: Jun. 15, 2006

(65) Prior Publication Data

US 2007/0289394 A1  Dec. 20, 2007

(51) Int. Cl.
*G01N 1/22* (2006.01)
(52) U.S. Cl. .................................... 73/863.21
(58) Field of Classification Search .............. 73/863.21, 73/61.71, 61.72; 134/18, 34, 32, 57 R
See application file for complete search history.

(56) References Cited

U.S. PATENT DOCUMENTS

| 3,890,844 | A | * | 6/1975 | Gale | 73/864.33 |
| 4,347,749 | A | * | 9/1982 | Heintze | 73/863.21 |
| 5,368,054 | A | * | 11/1994 | Koretsky et al. | 134/153 |
| 5,989,355 | A | | 11/1999 | Brandt et al. | 134/6 |
| 6,281,020 | B1 | | 8/2001 | Usui | 436/175 |
| 6,449,123 | B1 | | 9/2002 | Tsujimoto et al. | 360/125.38 |
| 6,810,887 | B2 | | 11/2004 | Tan | 134/1.3 |
| 6,923,188 | B2 | * | 8/2005 | Wen et al. | 134/22.18 |
| 2003/0179494 | A1 | | 9/2003 | Kaneko | 360/98.08 |
| 2006/0081521 | A1 | * | 4/2006 | Hjerpe et al. | 210/171 |
| 2008/0135065 | A1 | * | 6/2008 | Yao et al. | 134/18 |

FOREIGN PATENT DOCUMENTS

| JP | 1025385 | 1/1989 |
| JP | 2285635 | 11/1990 |
| JP | 6258202 | 9/1994 |
| JP | 8045888 | 2/1996 |
| JP | 9005227 | 1/1997 |
| JP | 2002011419 | 1/2002 |
| JP | 2002025049 | 1/2002 |

OTHER PUBLICATIONS

"Contactless Scrubber-A Disk Cleaning Device", *IBM Technical Disclosure Bulletin*, (Jan. 1982),p. 4023.
"Method of Quantitatively Detecting Particles On Surfaces", *IBM Technical Disclosure Bulletin*, (Nov. 1986).
"Wafter Cleaner by Use of High Pressure Pulsating Liquid", *IBM Technical Disclosure Bulletin*, (Apr. 1978),p. 4331.

\* cited by examiner

*Primary Examiner*—Hezron Williams
*Assistant Examiner*—Tamiko D Bellamy

(57) ABSTRACT

A system and method for using a spray/liquid particle count (LPC) to measure particulate contamination is disclosed. Initially, a component for particulate extraction is received. A sprayer is provided for spraying a liquid on the component. In addition, a container is provided for catching the liquid spraying on the component. The container is clean prior to receiving the liquid and the liquid is collected for later analysis of a number of particles extracted from the component.

18 Claims, 8 Drawing Sheets

Background

Background

500

550

SYSTEM AND METHOD FOR USING A SPRAY/LIQUID PARTICLE COUNT (LPC) TO MEASURE PARTICULATE CONTAMINATION

TECHNICAL FIELD

The present invention relates generally to particulate contamination measurement, and more particularly to a system and method for using a spray/liquid particle count (LPC) to measure particulate contamination.

BACKGROUND ART

Hard disk drives are used in almost all computer system operations. In fact, most computing systems are not operational without some type of hard disk drive to store the most basic computing information such as the boot operation, the operating system, the applications, and the like. In general, the hard disk drive is a device which may or may not be removable, but without which the computing system will generally not operate.

The basic hard disk drive model includes a storage disk or hard disk that spins at a designed rotational speed. An actuator arm is utilized to reach out over the disk. The arm carries a head assembly that has a magnetic read/write transducer or head for reading/writing information to or from a location on the disk. The transducer is attached to a slider, such as an air-bearing slider, which is supported adjacent to the data surface of the disk by a cushion of air generated by the rotating disk. The transducer can also be attached to a contact-recording type slider. In either case, the slider is connected to the actuator arm by means of a suspension. The complete head assembly, e.g., the suspension and head, is called a head gimbal assembly (HGA).

In operation, the hard disk is rotated at a set speed via a spindle motor assembly having a central drive hub. Additionally, there are tracks evenly spaced at known intervals across the disk. When a request for a read of a specific portion or track is received, the hard disk aligns the head, via the arm, over the specific track location and the head reads the information from the disk. In the same manner, when a request for a write of a specific portion or track is received, the hard disk aligns the head, via the arm, over the specific track location and the head writes the information to the disk.

Over the years, the disk and the head have undergone great reductions in their size. Much of the refinement has been driven by consumer demand for smaller and more portable hard drives such as those used in personal digital assistants (PDAs), MP3 players, and the like. For example, the original hard disk drive had a disk diameter of 24 inches. Modern hard disk drives are much smaller and include disk diameters of less than 2.5 inches (micro drives are significantly smaller than that). Advances in magnetic recording are also primary reasons for the reduction in size.

This continual reduction in size has placed steadily increasing demands on the technology used in extracting particulate from the hard disk drive and the components thereof. For example, particulate contamination has been one of the major contaminations encountered in HDD (Hard Disk Drive) industries, on its components, in its assembly processes.

Presently, as shown in background FIG. 1a, US/LPC (Ultrasonic Extraction/Liquid Particle Count) is a well established LPC method for extracting particulates from components of a HDD. Moreover, US/LPC has been widely used in HDD industries for many years.

In general, the US/LPC 100 method includes providing a tank 120 with a liquid 125 therein. A container 105, filled with an amount of extracting liquid 115 and the component 110, is placed into the tank 120. Ultrasonic energy is then provided to the liquid 125 in tank 120. The ultrasonic energy transfers through the liquid 125 and into the extracting liquid 115 in container 105. The component 110 is ultrasonically extracted and the extracting liquid 115 receives the removed particles. The particle filled liquid 115 is then taken for LPC. The particle sized detected can be 2 um, 0.5 um, 0.3 um or 0.2 um, or smaller; and the Ultrasonic Frequency commonly used can be one of the following: 40, 68, 80, 120, 132, 140, 170, 192, 220, 270 kHz, or even high frequencies.

However, the ultrasonic extraction method is extremely stressful on the component 110 during the extraction process. That is, the number of particles that are found after extracting, via the LPC, is high and is mainly due to the ultrasonic energy eroding connected base material, rather than removing loose particles, from the component 110.

For example, FIG. 1b provides a graph of particles found after ultrasonically extracting a component 160 without a scratch and an equivalent component 170 with 4 lines of scratches. From the graph 150, it is apparent that there is no significant deviation between the two components 160 and 170. In other words, the component 160 with no scratches provides a statistically similar number of particles as the component 170 with four lines of scratches.

Therefore, what is needed is a gentle extraction method for utilization on HDD components, subassemblies, whole drive, tools/jigs, HDD consumables, and any other non HDD items which require particle extracting.

SUMMARY

A system and method for using a spray/liquid particle count (LPC) to extract particulate from a component is disclosed. Initially, a component for particulate extraction is received. A sprayer is provided for spraying a liquid on the component. In addition, a container is provided for catching the liquid spraying on the component. The container is clean prior to receiving the liquid and the liquid is collected for later analysis of a number of particles extracted from the component

BRIEF DESCRIPTION OF THE DRAWINGS

Background

Background

DETAILED DESCRIPTION

Reference will now be made in detail to the alternative embodiment(s) of the present invention. While the invention will be described in conjunction with the alternative embodiment(s), it will be understood that they are not intended to limit the invention to these embodiments. On the contrary, the invention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, and components have not been described in detail as not to unnecessarily obscure aspects of the present invention.

The discussion will begin with an overview of a hard disk drive and components connected therewith. The discussion will then focus on a physical description of the spray/liquid particle count (LPC) component particulate extractor apparatus. Finally, an exemplary method for using a spray/liquid particle count (LPC) to measure particulate contamination will be described.

The method will provide a spray/LPC system that is able to sensitively detect and remove surface loose particles on a component without removing significant amounts of attached base components. In other words, the spray/LCP method and system described herein will extract loose particles without significantly removing attached particles from the components. As is well known, the most harmful particles, e.g., particles that will detrimentally effect overall operation of an assembly using the component, are the loose particles.

Overview

Figure 2:
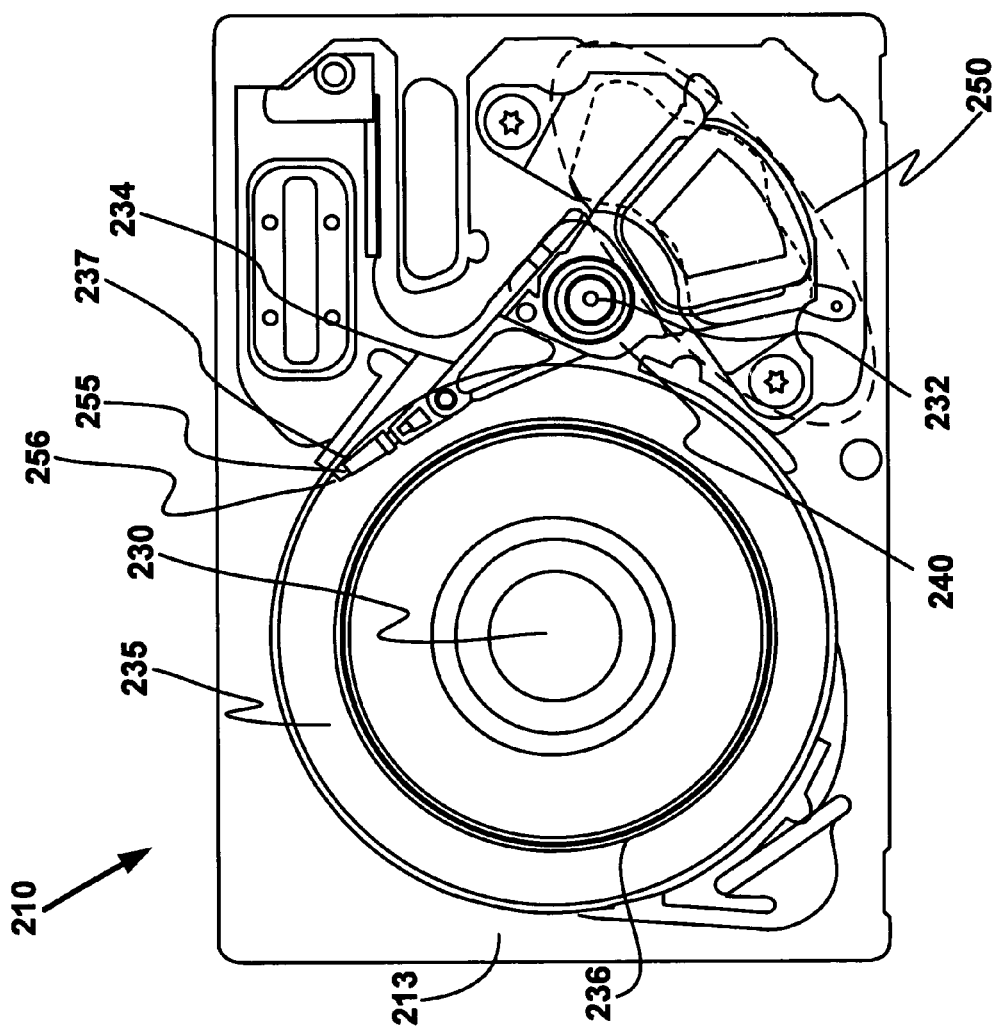
FIG. 2 is a plan view of an HDD with cover and top magnet removed in accordance with one embodiment of the present invention.

With reference now to FIG. 2, a plan view of an HDD with cover and top magnet removed is shown in accordance with one embodiment of the present invention. FIG. 2 illustrates the relationship of components and sub-assemblies of HDD 210 and a representation of data tracks 236 recorded on the disk surfaces 235 (one shown). The cover is removed and not shown so that the inside of HDD 210 is visible. The components are assembled into base casting 213, which provides attachment and registration points for components and sub-assemblies.

A plurality of suspension assemblies 237 (one shown) are attached to the actuator arms 234 (one shown) in the form of a comb. A plurality of transducer heads or sliders 255 (one shown) are attached respectively to the suspension assemblies 237. Sliders 255 are located proximate to the disk surfaces 235 for reading and writing data with magnetic heads 256 (one shown). The rotary voice coil motor 250 rotates actuator arms 234 about the actuator shaft 232 in order to move the suspension assemblies 237 to the desired radial position on disks 212. The actuator shaft 232, hub 240, actuator arms 234, and voice coil motor 250 may be referred to collectively as a rotary actuator assembly.

Data is recorded onto disk surfaces 235 in a pattern of concentric rings known as data tracks 236. Disk surface 235 is spun at high speed by means of a motor-hub assembly 230. Data tracks 236 are recorded onto spinning disk surfaces 235 by means of magnetic heads 256, which typically reside at the end of sliders 255. FIG. 2 being a plan view shows only one head, slider, and disk surface combination. One skilled in the art understands that what is described for one head-disk combination applies to multiple head-disk combinations, such as disk stacks (not shown). However, for purposes of brevity and clarity, FIG. 2 only shows one head and one disk surface.

Figure 3:
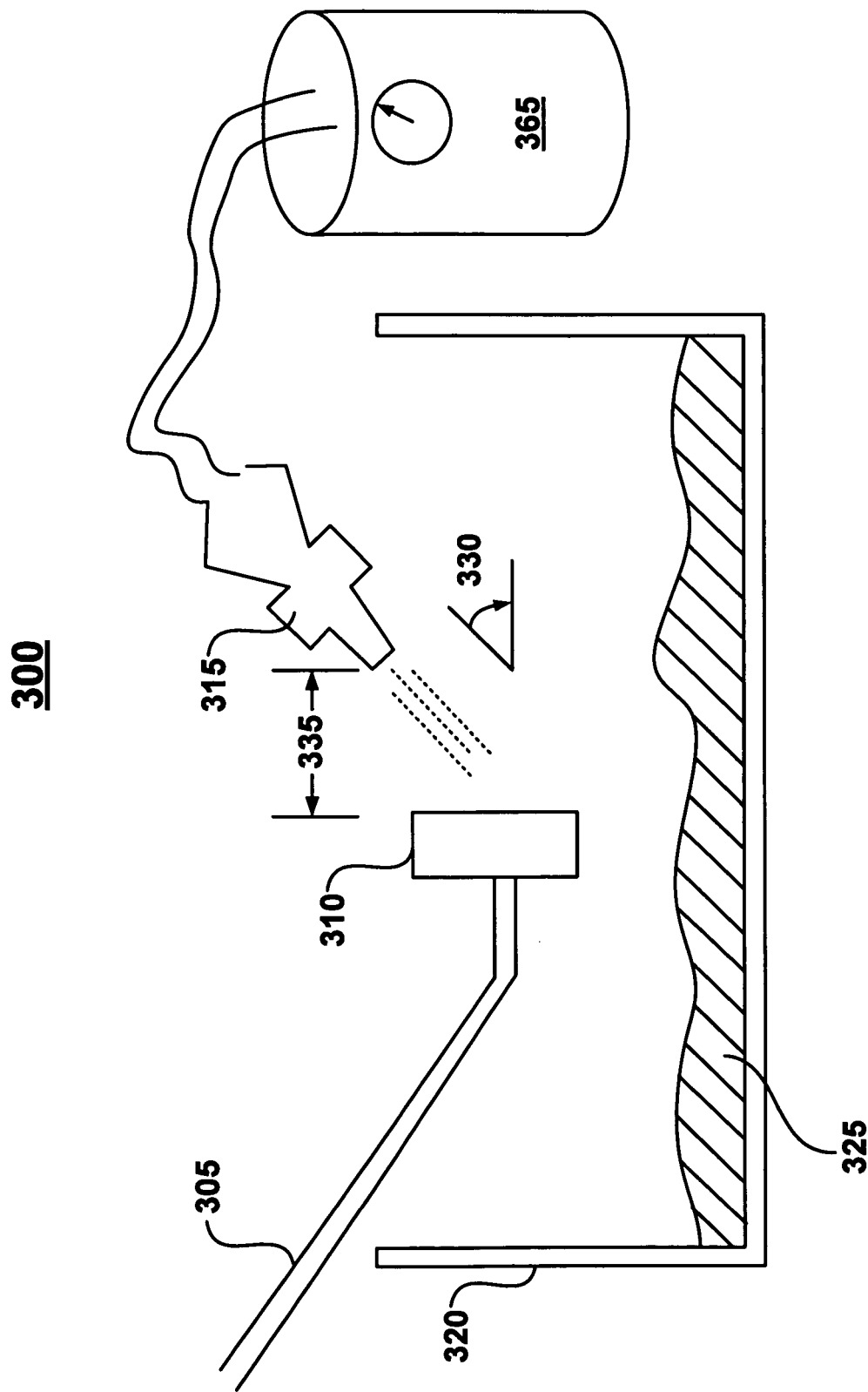
FIG. 3 is an exemplary block diagram of a Spray/LPC apparatus in accordance with one embodiment of the present invention.

Referring now to FIG. 3, an exemplary block diagram of a Spray/LPC apparatus 300 is shown in accordance with one embodiment of the present invention. In one embodiment, spray/LPC 300 includes an arm 305 for supporting a component 310 over a container 320. In addition, spray/LPC 300 includes a sprayer 315, a pressurized container 365, and fluid 325 which is the fluid collected after being sprayed on component 310 from sprayer 315. Spray/LPC also illustrates an adjustable angle of spray 330 and an adjustable standoff distance 335.

Figure 4:
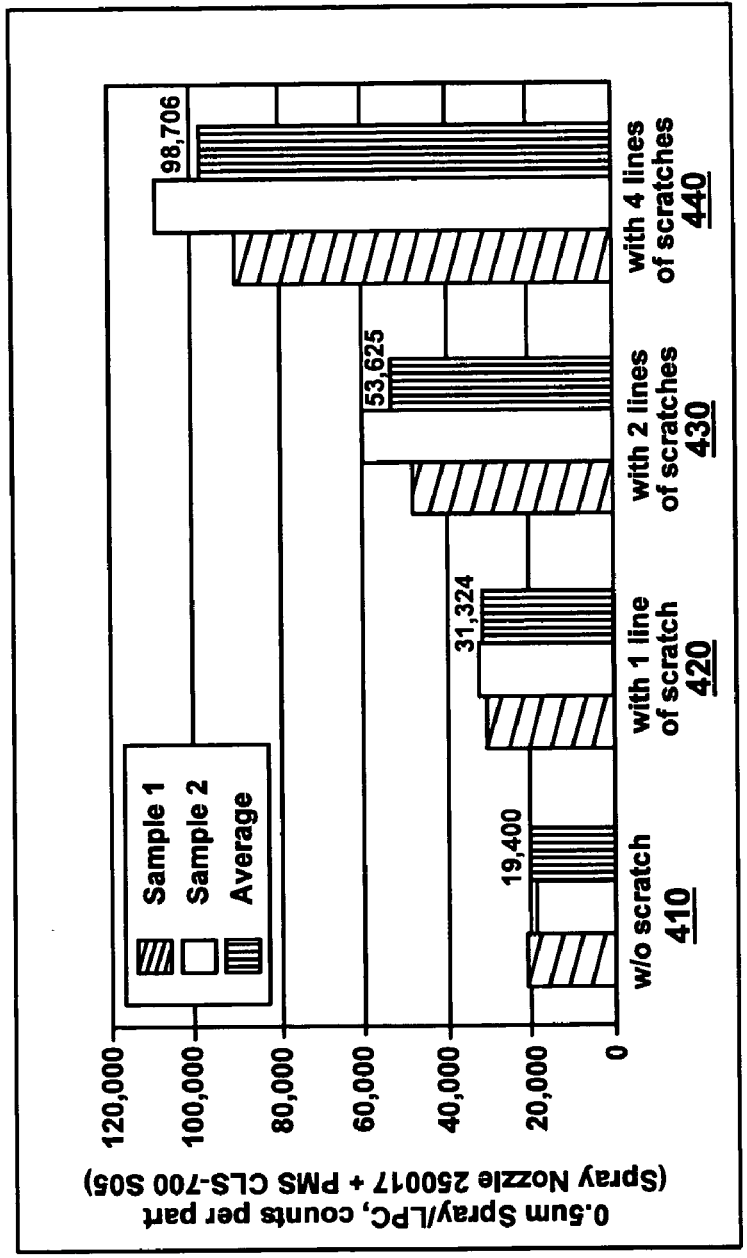
FIG. 4 is a graph of four similar components with a different number of scratches per component and the resulting particulate extraction realized when utilizing a spray/LPC apparatus in accordance with one embodiment of the present invention.

With reference now to FIG. 4, a graph 400 of four similar components with a different number of scratches per component and the resulting particulate extraction realized when utilizing a spray/LPC apparatus 300 is shown in accordance with one embodiment of the present invention. Specifically, graph 400 provides a first component 410 with no scratches, a second component 420 with one scratch line, a third component 430 with two lines of scratches and a fourth component 440 with 4 lines of scratches. As is clearly shown, the graph 400 includes two samples and an average for each of the four test cases.

Figure 1A:
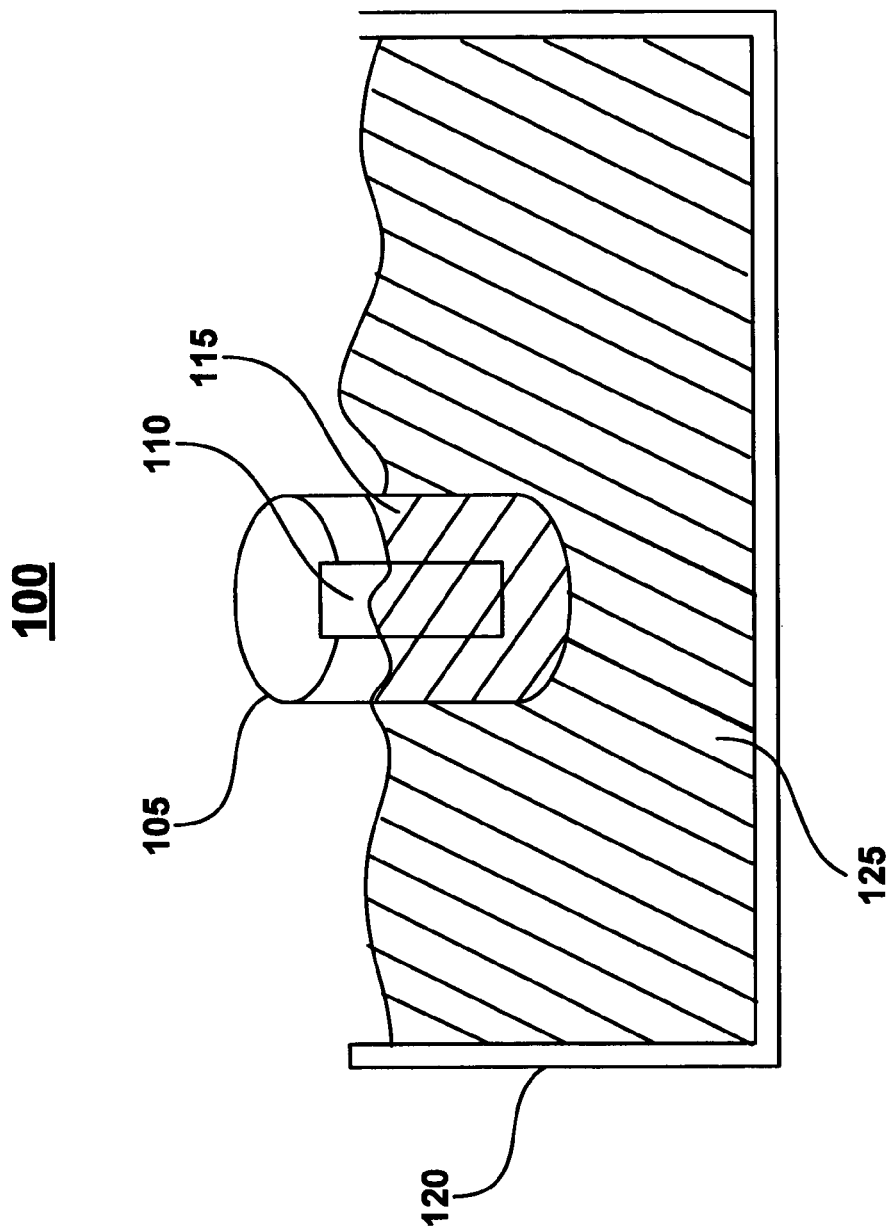
FIG. 1a is an exemplary block diagram of a US/LPC (Ultrasonic Extraction/Liquid Particle Count) apparatus.
Figure 1B:
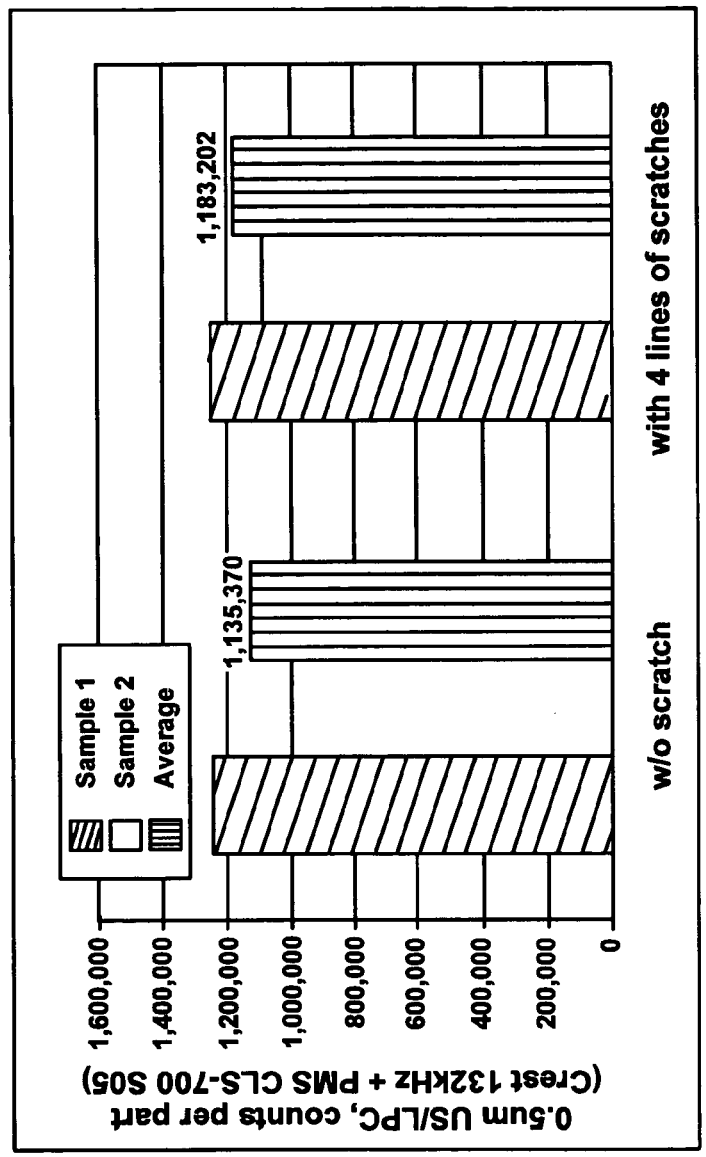
FIG. 1b is a graph of two components with a different number of scratches with particulate extracted via a US/LPC apparatus.

At graph 400, a linear relationship can be clearly seen between the four distinct scratch cases. This spray/LPC linear relationship is in direct contrast to graph 150, of FIG. 1b, where the ultrasonic extractor provided no significant statistical difference between a component 160 with no scratches and a component 170 with four scratches.

Not only does the graph 400 provide a linear relationship based on the number of scratches (e.g., number of loose particles) but the graph 400 also shows a significant reduction in the overall number of particles removed from the components. For example, in graph 150, the component with no scratches provided an average 1,135,370 particles after ultrasonic extracting. However, in graph 400, the worst case 4 scratch average was only 98,706 particles after spray extracting. This is a difference of over one million particles.

Thus, graph 400 in comparison with graph 150 clearly illustrates that the spray/LPC method described herein significantly reduces the wear on the components. That is, unlike ultrasonic extracting, the spray extracting does not significantly degrade the component. Additionally, the spray/LPC extracting does not significantly remove base particles still connected to the component. Instead, the spray/LPC extracting removes loose particles in a linear and repeatable fashion.

Figure 5A:
FIG. 5a is an exemplary flat fan spray pattern in accordance with one embodiment of the present invention.
Figure 5B:
FIG. 5b is an exemplary conical spray pattern in accordance with one embodiment of the present invention.

Referring now to FIG. 5a, an exemplary flat fan spray pattern 500 is shown in accordance with one embodiment of the present invention. With reference now to FIG. 5b, an exemplary conical spray pattern 550 is shown in accordance with one embodiment of the present invention. The details of the spray patterns including pattern 500 and 550 are described in more detail herein. Moreover, they are provided herein merely for purposes of brevity and clarity. They are not meant to infer that they are the only available spray patterns.

Figure 6:
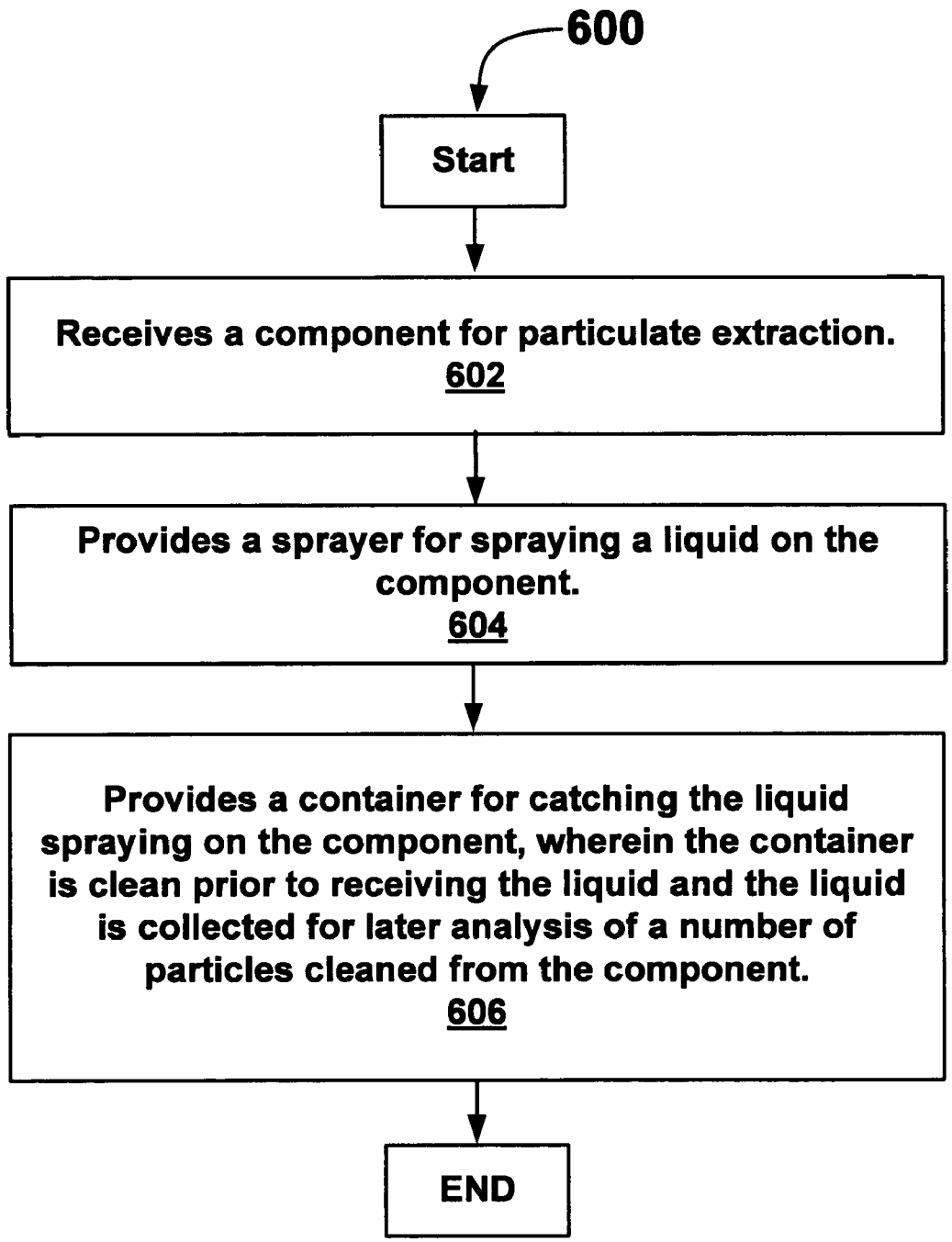
FIG. 6 is a flowchart of an exemplary method for using a spray/liquid particle count (LPC) to extract particulate from a component in accordance with one embodiment of the present invention.

Referring now to FIG. 6 and to FIG. 3, a flowchart 600 of an exemplary method for using a spray/liquid particle count (LPC) apparatus 300 to extract particulate and measure particulate contamination of a component is shown in accordance with one embodiment of the present invention. In general, the spray/LPC 300 extraction described herein is used to sensitively detect and remove particulate contamination or quality problems such as scratches, burrs, improper handling, and the like. This extracting results in loose particles being sensitively removed from the component 310 without aggressively over extracting particulate from the component 310.

With reference now to 602 of FIG. 6 and to FIG. 3, one embodiment receives a component 310. In one embodiment, the component 310 is a component in a hard disk drive (HDD). However, in another embodiment, the component 310 is a HDD subassembly, an entire HDD, a tool or jig associated with a HDD, and HDD consumables. In yet another embodiment, the component 310 is not associated with a HDD. For example, the component 310 may be a component from the semiconductor industry, or the like. As shown in FIG. 3, the component 310 is supported in the proper position within the spray/LPC apparatus 300 by the supporting arm 305.

Referring now to 604 of FIG. 6 and to FIG. 3, one embodiment provides a sprayer 315 for spraying a liquid 325 on the component 310. The sprayer 315 may be any of a number or liquid spraying systems. For example, in FIG. 3, the sprayer 315 is connected to a pressurized tank 365 to form the spraying system. However, it is understood that the spraying system can be any of a plurality of spraying methods such as a pressurized system, a gravity fed system, and the like. The use of a pressurized system is described herein merely for purposes of brevity and clarity.

In one embodiment, the sprayer 315 includes a nozzle having a full cone spray pattern 550, as shown in FIG. 5b, for spraying the liquid 325 on the component 310. In another embodiment, the sprayer 315 includes a nozzle having a flat fan spray pattern 500, as shown in FIG. 5a, for spraying the liquid 325 on the component 310. Although two spray patterns are described, it is understood that the provided patterns are exemplary. That is, the present invention is well suited to a plurality of spray patterns. The use of the approximate numbers provided herein is merely for purposes of brevity and clarity.

For example, tables 1, 2 and 3 provide an overview of the spray nozzle impact characteristics.

TABLE 1 for a fixed nozzle, impact is proportional to the liquid pressure or spray flowrate.

| Component | Nozzle | Spray/LPC (>2 um per part) @ 40 psi (350 ml/mm) | Spray/LPC (>=2 um per part) @ 60 psi (440 ml/mm) | Impact @ 60 psi Vs Impact @ 40 psi |
|---|---|---|---|---|
| Part A | 6501 Flat Fan Spray | 9916 | 12507 | |
| | | 9297 | 12004 | |
| | | 10024 | | |
| Avg | | 9747 | 12256 | 26% higher |

TABLE 2 for different capacity but same type of nozzles, impact is not a function of spray flowrate.

| Component | Nozzle | Spray/LPC (>2 um per part) by 6501 (440 ml/mm @ 60 psi) | Spray/LPC (>=2 um per part) by 3404K643 (1600 ml/min @ 60 psi) | Impact @ 3404K643 Vs Impact @ 6501 |
|---|---|---|---|---|
| Part A | 6501 Flat Vs 3404K643 Flat | 12507 | 9125 | |
| | | 12004 | 7950 | |
| Avg | | 12256 | 8538 | 30% lower |

TABLE 3 for different types of nozzles, impact is not a function of spray flowrate.

| Component | Nozzle | Spray/LPC (>2 um per part) by 6501 (350 mi/mm @ 40 psi) | Spray/LPC (>=2 um per part) by M6 (350 mi/mm @ 40 psi) | Impact @ M6 Vs Impact @ 6501 |
|---|---|---|---|---|
| Part A | 6501 Flat Vs M6 Fine | 10757 | 7115 | |
| | | 9752 | 7154 | |
| | | 10238 | 7202 | |
| | | 10249 | 7157 | 30% lower |

In one embodiment, the sprayer 315 sprays distilled water on the component 310. That is, only distilled water is sprayed from the sprayer 315 onto the component 310. In another embodiment, approximately a 0.004% micro 90 detergent is provided to the distilled water for spraying on the component 310. The detergent is utilized to aid in extracting particulate from a component 310. Although an approximate detergent mix is described herein, it is understood that the provided percentage is exemplary. That is, the present invention is well suited to a plurality of detergent mixes. The use of the approximate number provided herein is merely for purposes of brevity and clarity.

For example, table 4 provides an overview of the effects of detergent and its concentration on the impact of a nozzle.

TABLE 4

| Nozzle and Spray Condition | Part | Spray/LPC (>2 um per part) of Component B |
|---|---|---|
| 250017 Flat Fan spray @ 4 opsi Pure DIW | Part #1 | 6435 |
| | Part #2 | 5562 |
| | Average | |
| 250017 Flat Fan spray @ 4 opsi 0.004% Detergent | Part #1 | 7526 |
| | Part #2 | 6722 |
| | Average | 7124 |
| 250017 Flat Fan spray @ 4 opsi 0.04% Detergent | Part #1 | 12849 |
| | Part #2 | 13245 |
| | Average | 13047 |

Although detergent can help enhance the nozzle's spray impact, high concentrations of detergent may cause unwanted air bubbles. Therefore, in one embodiment, a very low level of detergent is utilized to enhance the particle removal from the component's surface.

The sprayer also utilizes approximately a 25 degree angle of spray 330 between the sprayer and the component, in one exemplary embodiment. In another embodiment, approximately a one inch standoff 335 is utilized between the sprayer 315 and the component 310 receiving the particle extraction. In yet another embodiment, approximately a 65 milliliter per minute flow rate at approximately 40 pounds per square inch pressure is utilized. Although an angle of spray 330, standoff 335 and pressure are provided herein, it is understood that the provided numbers are exemplary. That is, the present invention is well suited to a plurality of pressures, angles and standoffs alone and in combination as shown in the following tables based on spray pattern, component being extracted, use of detergent, and the like. The use of the approximate numbers herein is merely exemplary embodiments provided for purposes of brevity and clarity.

For example, table 5 provides an overview of the effect of different praying distances (>=2 um per part).

Referring now to 606 of FIG. 6 and to FIG. 3, one embodiment provides a container 320 for catching the liquid 325 spraying on the component, wherein the container 320 is clean prior to receiving the liquid 325 and the liquid is collected for later analysis of a number of particles extracted from the component 310. In one embodiment, a beaker is used as the container 320 for catching the liquid 325 sprayed on the component 310.

For example, in one exemplary embodiment, the sprayer 315 sprays liquid 325 onto component 310 for 1-3 minutes depending on the size, surface area, complexity of parts or subassemblies, and the like. After the spraying is stopped and the particles on the component 310 have been extracted, the fluid 325 collected in the container 320 is then processed by a LPC to establish the particle count. That is, the particles washed from component 310 are counted by performing a particle count on the now contaminated liquid 325.

Thus, embodiments of the present invention provide a system and method for using a spray/liquid particle count (LPC) to measure particulate contamination. Moreover, embodiments provide a system and method for using a spray/liquid particle count (LPC) to measure particulate contamination that significantly reduces the number of attached particles being unnecessarily removed from the component. Additionally, embodiments provide a system and method for using a spray/liquid particle count (LPC) to measure particulate contamination that significantly protects the component from damage during the extraction process. In so doing, particulate from the component is more quickly, efficiently, and properly extracted while deleterious over extracting effects, such as extracting damage or stresses on the component are reduced.

While the method of the embodiment illustrated in flowchart 600 show specific sequences and quantity of steps, the present invention is suitable to alternative embodiments. For example, not all the steps provided for in the methods are required for the present invention. Furthermore, additional steps can be added to the steps presented in the present embodiment. Likewise, the sequences of steps can be modified depending upon the application.

The alternative embodiment(s) of the present invention, a system and method for using a spray/liquid particle count (LPC) to measure particulate contamination is thus described. While the present invention has been described in particular embodiments, it should be appreciated that the present invention should not be construed as limited by such embodiments, but rather construed according to the below claims.

What is claimed is:

1. A method for using a spray/liquid particle count (LPC) to measure particulate contamination, said method comprising:
   receiving a component from a hard disk drive as said component for particulate extraction;
   providing a sprayer for spraying a liquid on said component; and

TABLE 5

| Spraying Distance | Part Name | Part #1 | Part #2 | Part #3 | Part #4 | Part #5 | Average | Std Dev |
|---|---|---|---|---|---|---|---|---|
| 15 mm | Part C | 4792 | 4922 | 5172 | 5263 | 5287 | 5087 | 219 |
| 25 mm = 1 inch | Part C | 3861 | 4316 | 4418 | 4463 | 4623 | 4336 | 288 |
| 15 vs. 25 mm Particle Reduction | | 19% | 12% | 15% | 15% | 13% | 15% | | providing a container for catching said liquid spraying on said component, wherein said container is clean prior to receiving said liquid and said liquid is collected for later analysis of a number of particles extracted from said component.

2. The method of claim 1 wherein said sprayer further comprises:
utilizing a nozzle providing a full cone spray pattern for spraying said liquid on said component.

3. The method of claim 1 wherein said sprayer further comprises:
utilizing a nozzle providing a flat fan spray pattern for spraying said liquid on said component.

4. The method of claim 1 further comprising:
utilizing distilled water as said liquid for spraying on said component.

5. The method of claim 4 further comprising:
providing approximately a 0.004% micro 90 detergent to said distilled water for spraying on said component.

6. The method of claim 1 wherein further comprising:
utilizing approximately a 25 degree angle of spray between said sprayer and said component for particulate extraction.

7. The method of claim 1 further comprising:
utilizing approximately a 1 inch standoff between said sprayer and said component for particulate extraction.

8. The method of claim 1 further comprising:
utilizing approximately a 65 milliliter per minute flow rate at approximately a 40 pounds per square inch pressure.

9. The method of claim 1 further comprising:
utilizing a beaker as said container for catching said liquid spraying on said component.

10. A spray/liquid particle count (LPC) component particulate extractor for extracting particulate from a component of a hard disk drive comprising:
a retaining mechanism for receiving a hard disk drive component for particulate extraction;
a sprayer for providing a stream of spraying liquid to said hard disk drive component; and
a container for catching said liquid spraying on said hard disk drive component, wherein said container is clean prior to receiving said liquid, wherein said liquid is provided to an LPC analyzer for counting a number of particles extracted from said hard disk drive component.

11. The spray/LPC component particulate extractor of claim 10 wherein said stream of spraying liquid sprayed from said sprayer is received from a pressurized container.

12. The spray/LPC component particulate extractor of claim 10 wherein said sprayer utilizes a nozzle providing a full cone spray pattern for spraying said liquid on said component.

13. The spray/LPC component particulate extractor of claim 10 wherein said sprayer utilizes a nozzle providing a flat fan spray pattern for spraying said liquid on said component.

14. The spray/LPC component particulate extractor of claim 10 wherein distilled water is utilized as said liquid for spraying on said component.

15. The spray/LPC component particulate extractor of claim 14 wherein approximately a 0.004% micro 90 detergent is provided to said distilled water for spraying on said component.

16. The spray/LPC component particulate extractor of claim 10 wherein said sprayer comprises:
an approximate 25 degree angle of spray between said sprayer and said component for particulate extraction; and
an approximately 1 inch standoff between said sprayer and said component for particulate extraction.

17. The spray/LPC component particulate extractor of claim 16 wherein said sprayer further comprises:
an approximately 65 milliliter per minute flow rate at approximately a 40 pounds per square inch pressure is utilized.

18. The spray/LPC component particulate extractor of claim 10 further comprising:
utilizing a beaker as said container for catching said liquid spraying on said component.

* * * * *